United States Patent [19]
Trost

[11] Patent Number: 5,321,715
[45] Date of Patent: Jun. 14, 1994

[54] LASER PULSE FORMAT FOR PENETRATING AN ABSORBING FLUID

[75] Inventor: David Trost, San Francisco, Calif.
[73] Assignee: Coherent, Inc., Santa Clara, Calif.
[21] Appl. No.: 57,125
[22] Filed: May 4, 1993
[51] Int. Cl.⁵ ............................................... H01S 3/09
[52] U.S. Cl. ......................................... 372/69; 372/70; 372/51; 372/6; 372/25; 372/39; 128/633
[58] Field of Search ................. 372/39, 6, 25, 69, 78; 128/303.1

[56] References Cited
U.S. PATENT DOCUMENTS
4,875,214 10/1989 Denne ........................... 372/5

Primary Examiner—Léon Scott, Jr.
Attorney, Agent, or Firm—Limbach & Limbach

[57] ABSTRACT

A pulse format for a laser system is disclosed for maximizing the energy delivered to a target immersed in an absorbing liquid. A first pulse is generated having an energy sufficient to initiate the formation of a vapor bubble in the liquid medium adjacent the end of the delivery device. A second, high energy pulse is generated after the vapor bubble initiated by the first pulse has expanded an amount sufficient to displace the liquid between the delivery device and the target. In this manner, the second pulse is delivered directly to the target and little energy is lost to the liquid medium.

37 Claims, 1 Drawing Sheet

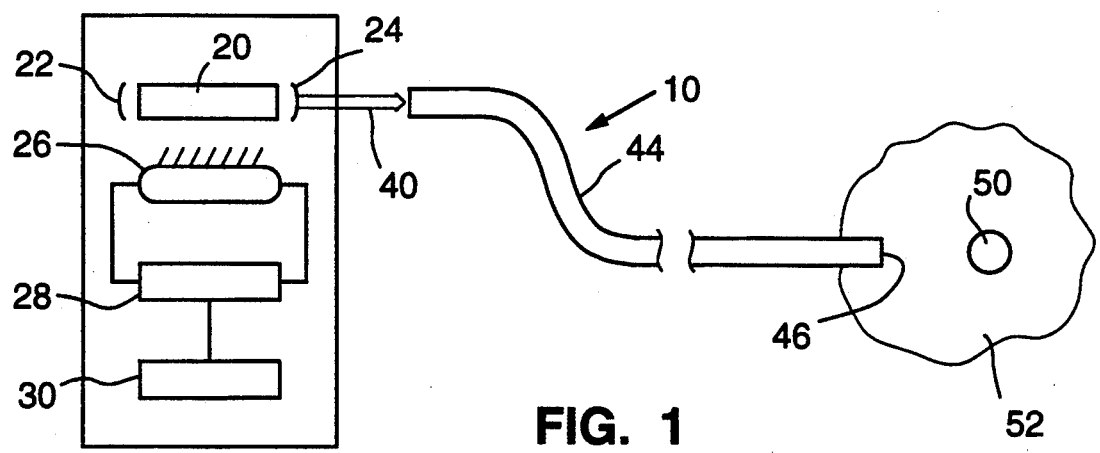
FIG. 1
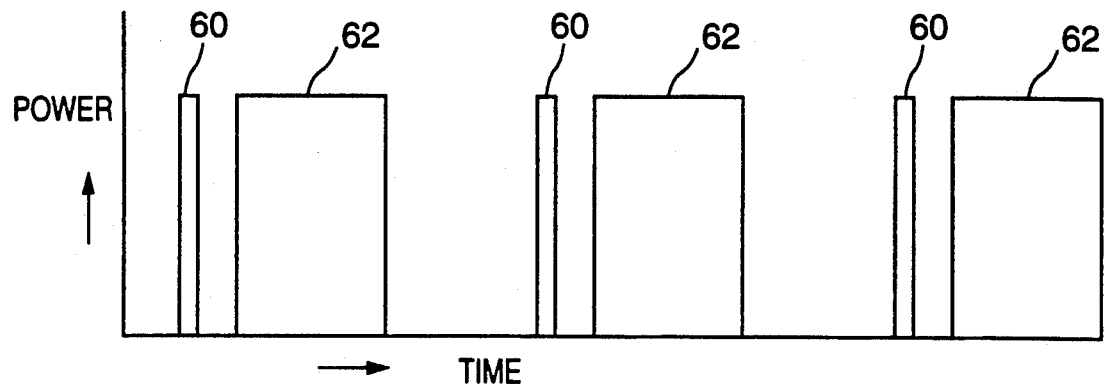
FIG. 2
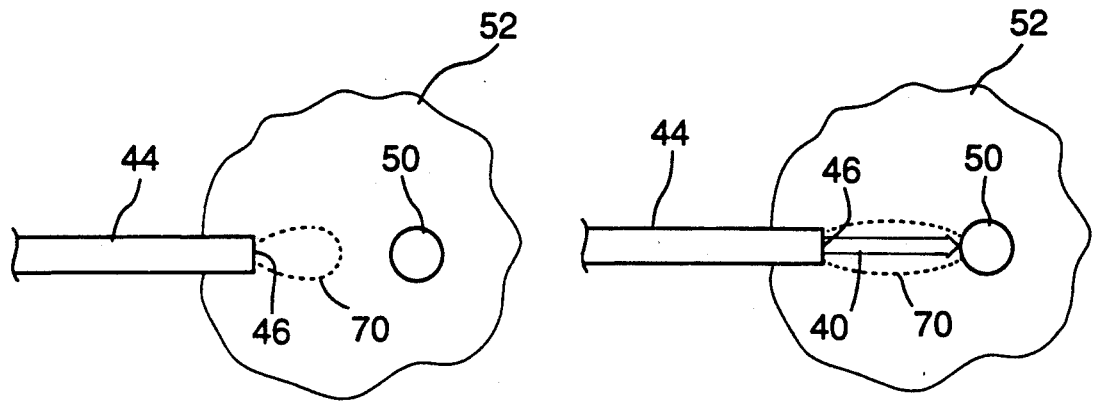
FIG. 3  FIG. 4

LASER PULSE FORMAT FOR PENETRATING AN ABSORBING FLUID

TECHNICAL FIELD

The subject invention relates to the control of a pulsed laser system for improving the delivery of energy to a target immersed in an absorbing fluid. The invention is particularly useful in medical systems where the tissue to be treated is immersed in a fluid field.

BACKGROUND OF THE INVENTION

Within the last decade, there have been significant advances made in the application of lasers in medicine. A variety of different types of lasers are now being used in a variety of different procedures.

One such laser system is marketed by the assignee herein under the trademark Versapulse. This system includes a laser having a gain medium formed from Holmium:YAG which generates an output wavelength of 2.1 microns. The output of the laser is delivered to the treatment site via an optical fiber. The laser system has been found to be extremely useful in a variety of orthopedic applications such a knee surgery.

In many of these orthopedic applications, the tissue to be treated is immersed in a liquid medium such as saline which primarily consists of water. The 2.1 micron wavelength output of the Ho:YAG laser is highly absorbed in water. Thus, it would be expected that a large portion of the energy emitted from the fiber would be absorbed in the liquid medium before reaching the target tissue. In fact, only a portion of the laser light is absorbed in the liquid medium due to a phenomenon referred to as the "Moses effect."

One of the earliest reports of the Moses effect in association with Ho:YAG lasers appeared in an article by van Leeuwen, et. al., in *Lasers in Surgery and Medicine*, ("Non-contact Tissue Ablation by holmium:YSGG Laser Pulses in Blood," Vol. 11, 1991). In this article, it was reported that when the laser energy is absorbed in the liquid medium, a vapor bubble is created which expands outwardly towards the target tissue. Once the bubble reaches the target, the laser beam can pass through the vapor to the target with very little attenuation since the density of the water molecules in the steam is many orders of magnitude less than in the liquid state.

In this initial report, it was noted that the bubble formed on time scale on the order of 100 to 200 microseconds and lasted for a few hundred microseconds more before collapsing. These time frames are on the order of the pulse widths used with the solid state holmium laser. Thus, it was initially assumed that a large portion of the pulse was necessary to form the bubble and to maintain its existence before collapsing.

In a recent presentation, the same researchers reported that the formation of the vapor bubble was not dependent upon the generation of a standard, high energy, holmium laser pulse. In contrast, the researchers found that the vapor bubble can be initiated with a very small amount of laser energy. In addition, the speed at which the bubble forms is relatively independent of the duration or excess energy in the pulse. (See, "Bubble Formation During Pulsed Laser Ablation: Mechanism and Implications", SPIE Conference on Biomedical Optics, Los Angeles, van Leeuwen et. al., Jan. 18, 1993, as yet unpublished in written form)

Based on these measurements, the researchers concluded that the vapor bubble can be formed without having to vaporize all of the liquid medium in the region in front of the delivery end of the fiber. Under normal circumstances, in order to vaporize water, its temperature must first be raised from ambient temperature to the boiling point (ie. 100 degrees centigrade). Once the temperature of the water has been raised to the boiling point, the liquid can then be converted to a gas by supplying sufficient additional energy to overcome the latent heat of vaporization. This additional energy is about an order of magnitude greater than the energy necessary to raise the temperature of the water from body temperature to the boiling point.

The amount of energy be necessary to vaporize the water at the end of the fiber to create a vapor bubble is based on the specific heat of the water and the volume of the water in front of the fiber which is absorbing the light. The volume of water is defined by the cross-sectional area of the delivery end of the fiber multiplied by the absorption length of the laser wavelength in the water.

Based on their most recently recorded measurements, the prior researchers have concluded that the vapor bubble is created at an energy level significantly below that which would be needed to overcome the latent heat of vaporization for the volume of water which absorbs the laser light. Rather, it appears the energy required to form the vapor bubble roughly corresponds to the energy required to raise the temperature of the heated volume to the boiling point, which, as noted above, is an order of magnitude less than required to vaporize the volume.

It is believed by the applicant herein that the energy of the laser pulse functions to vaporize only a tiny fraction of the volume of liquid which is absorbing the laser radiation while the remainder of the volume is heated only to the boiling point. Once the tiny volume of fluid near the delivery end of the fiber has been vaporized, the bubble will begin to form and expand at a rate which is substantially independent of the duration and energy in the pulse.

SUMMARY OF THE INVENTION

The subject invention has been developed to take advantage of the discoveries discussed above. More specifically, a new laser pulse delivery format has been developed which will maximize the energy of the laser radiation reaching a target that is immersed in an absorbing liquid.

In the prior art approach, the Holmium laser was configured to generate a series of individual pulses. Each of the pulses was on the order of one joule having a pulse width on the order of 250 microseconds. Within about the first 50 milliseconds after the initiation of the pulse, the vapor bubble will begin to form. The bubble will grow to a millimeter in length within the first 100 microseconds of the pulse and to two millimeters in length within 200 microseconds. Before the vapor bubble reaches the target, one half or more of the energy in the laser pulse can be absorbed in the fluid. Once the vapor bubble reaches the target, substantially all of the remaining energy of the pulse will pass through the vapor and irradiate the target.

In order to insure that a much higher percentage of the laser energy reaches the target, a new pulse format has been developed which includes a first pulse having an energy level selected to initiate the formation of the vapor bubble. The energy level required for the initiation pulse is only a few percent of the energy level which can be generated by the laser.

The initiation pulse is then followed by a regular, high energy pulse. The time delay between the two pulses is selected to be sufficient so that the vapor bubble will have had a chance to expand and displace a substantial portion of the liquid medium in the region between the delivery end of the fiber and the target. The time delay will be dependent upon the spacing between the fiber and the target and can be on the order of 100 to 200 microseconds. As can be appreciated once the bubble is formed, virtually all of the energy from the main pulse can be delivered to the target. Since a relatively low energy pulse is used to create the bubble, very little energy is wasted in heating the water and most of the energy generated is used to treat the tissue.

The subject invention is not limited to solid state laser systems or medical applications. Rather, it can be implemented in any system where a fluid medium exists in a space between the delivery device and the target and wherein the fluid medium absorbs the laser wavelength. For example, the subject system can be used with a carbon dioxide laser for treating tissues immersed in water. In addition, the absorption in the liquid medium need not be by the liquid itself. For example, proteins dissolved in water are absorbed by ultraviolet light. An ultraviolet source can be used to create a vapor bubble in a liquid medium having dissolved protein matter.

Further objects and advantages of the subject invention will become apparent from the following detailed description, taken in conjunction with the drawings in which:

BRIEF DESCRIPTION OF THE DRAWINGS

FIG. 1 is schematic diagram of a typical laser system which has been adapted to utilize the pulse format of the subject invention for maximizing the delivery of energy to a target tissue immersed in an absorbing liquid.

FIG. 2 is a timing and power diagram illustrating the pulse format of the subject invention.

FIG. 3 is an illustration of the initiation of a vapor bubble caused by a first, low energy pulse.

FIG. 4 is an illustration of the delivery of a second, high energy pulse to the target tissue through the vapor bubble.

DETAILED DESCRIPTION OF THE PREFERRED EMBODIMENTS

FIG. 1 illustrates a conventional solid state medical laser system 10 which has been adapted to utilize the pulse format of the subject invention. The system 10 includes a solid state gain medium 20. One suitable gain medium is a Holmium:YAG rod of the type presently sold by the assignee herein in its Versapulse laser. The gain medium 20 is located in a resonant cavity defined by a high reflecting mirror 22 and an output coupler 24. The gain medium is excited by a flashlamp 26.

A power supply 28 is provided to energize the flashlamp. The power supply 28 will include capacitors and transistors for triggering the capacitors in a manner well known in the prior art. The operation of the power supply 28 is controlled by processor 30. In the assignee's existing system, the laser is capable of generated a sequence of pulses at a repetition rate of up to 22 hertz. The maximum energy per pulse is on the order of one to three joules. A typical pulse length is on the order of 250 microseconds.

The output beam 40 generated from the laser cavity is coupled into a flexible optical fiber 44. A typical optical fiber for transmitting Ho:YAG radiation at 2.1 microns is formed from silica and will have a diameter on the order of 0.5 mm. The delivery end 46 of the fiber is positioned by the surgeon near the tissue 50 to be treated. As noted above, in many procedures, the tissue is immersed in an absorbing fluid 52. This fluid might be supplied from an external saline irrigation system or might exist in situ, in the body cavity. Although other possibilities will be discussed below, the fluids encountered in most orthopedic applications consist primarily of water which is highly absorptive of the 2.1 micron radiation. The absorption length in water is on the order of 0.4 mm.

In many surgical procedures performed in a liquid field, there will be a space between the delivery end of the fiber and the target tissue. In practice, a surgeon will often position the end of the fiber a distance of one to two millimeters away from the treatment site. By spacing the fiber from the treatment site, the surgeon can take advantage of the divergence of the laser beam exiting the fiber to ablate a larger area of tissue. Thus, it is quite common for the distance between the delivery end of the fiber and the target to exceed the absorption length of the laser radiation in the fluid.

Under these circumstances, the initial energy in each pulse will be absorbed in the fluid. In the prior art systems, the energy will continue to be absorbed in the fluid until the vapor bubble has formed and extends to the target. It has been estimated that one half or more of the energy in the pulse is lost in this manner. Once the vapor bubble reaches the target, all of energy in the trailing end of the pulse will be delivered directly to the target.

In order to minimize the loss of energy which occurs when the radiation is absorbed in the water during the formation of the vapor bubble, a new pulse format has been developed. The pulse format is illustrated in FIG. 2. As seen therein, the new pulse format includes a first, short, low energy pulse 60, followed thereafter by a second, standard, high energy pulse 62. This sequence is repeated at a rate similar to the current repetition rate for the individual high energy pulses.

In accordance with the subject invention, the energy of the first pulse 60 is selected to be sufficient to initiate the formation of the vapor bubble. As noted in the recent work by Leeuwen, this energy can be quite small compared with the energy available from the laser system. The amount of energy required is roughly equal to the amount of energy needed to raise the volume of liquid adjacent to the delivery end of the fiber to its boiling point. This energy can be calculated with the following formula:

$$A * L * C * \Delta T = minimum\ energy \quad (1)$$

where A equals the cross-sectional area of the fiber (or other delivery device), L is the absorption length of the radiation in the liquid medium, C is the specific heat of the liquid medium and $\Delta T$ is the difference in temperature between the ambient temperature of the liquid medium and the boiling point temperature.

By way of example, a typical silica optical fiber used to deliver 2.1 micron laser radiation will have a diameter of 0.5 mm and therefore an area A of 0.196 mm$^2$. As noted above, the absorption length L of 2.1 micron radiation in water is 0.4 mm. The specific heat C of water is 1.0 calorie/degree-centigrade/cm$^3$. Body or ambient temperature is 37 degrees centigrade so that $\Delta T$ is 63 degrees(100−37). By multiplying these four values, the minimum energy required to initiate the formation of a vapor bubble can be determined. In this example, the minimum energy is $5 \times 10^{-3}$ calories or 0.02 joules. (1 calorie=4.186 joules).

As can be seen, the vapor bubble can be formed with only one to two percent of the energy which can be generated by the laser. The formation of the vapor bubble 70 is indicated in FIG. 3. The triggering of the second pulse 62 should occur after the vapor bubble has expanded an amount sufficient to displace a substantial portion of the fluid medium as shown in FIG. 4. At this stage, a high percentage of the energy of the second pulse can be delivered directly to the target 50 because the density of the water molecules in the vapor bubble is orders of magnitude less than the density of the water molecules in the liquid medium which has been displaced.

The period between the first and second pulses can be set based on the expansion rate of the bubble and the expected distance between the delivery end 46 of the fiber and the target 50. The prior articles cited above provide information about the expansion rate of the bubble. As an example, the bubble will expand to a distance of about one millimeter in 100 microseconds and to two millimeters in 200 microseconds. In the preferred embodiment, the period between the first and second pulses will be at least 50 microseconds and is preferably between 100 and 200 microseconds. It is expected that second pulse will prevent the vapor bubble from collapsing until that pulse is terminated.

Based on the prior research, it appears that the length of time required to form the vapor bubble is independent of the length of the pulse. Thus, it will still require several hundred microseconds to form the vapor bubble even if the initiation pulse is significantly shorter. Vapor bubble formation was observed with initiation pulses as short as 100 nanoseconds. It is expected that the initiation pulse used in the subject invention will be shorter than 100 microseconds and preferably shorter than 30 microseconds.

As seen in FIG. 2, the two pulse sequence is repeated at a rate typical for the standard prior art laser. Each pair of pulses will function as described above, with the first pulse 60 of the pair used to initiate the vapor bubble and the second pulse 62 delivering the energy to the target.

In order to implement the pulse format of the subject invention, the processor 30 will trigger the power supply 28 to deliver current to the flashlamp 26 sufficient to generate a short, low energy laser pulse 60. In order to generate this pulse, enough energy from the flashlamp must be absorbed by the rod 20 to initiate a low level of lasing. Much of this energy will not be needed for the low energy initiation pulse. Since the energy storage time of the Holmium:YAG material is on the order of 60 milliseconds, if the second pulse is triggered within 200 microseconds, a significant portion of the energy supplied by the flashlamp to the rod for the initiation pulse 60 will be available to form the second pulse 62. It should therefore be possible to generate a full energy, one joule, 250 microsecond second pulse 62, even though some energy from the power supply has been used to generate the initiation pulse 60.

As noted above, in this example the initiation pulse should be at least 0.02 joules and could be as large as 0.1 joules. It is expected that the energy of the second pulse will be at least an order of magnitude larger than the initiation pulse.

This pulse formatting technique will be useful with many kinds of laser systems. For example, there are many other solid state lasers that have been shown to be beneficial for medical applications. These would include lasers having gain media formed from materials such as Nd:YAG, Nd:YLF, Nd:YAP, Nd:YALO, Ho:YSGG, Ho:YLF and Er:YAG. These laser produce an output having wavelengths in the 1.0 to 3.0 micron wavelength range which are absorbed in water.

The invention can also be used with gas lasers. For example, the assignee herein markets a carbon dioxide surgical laser system under the trademark Ultrapulse. In this laser, the duration of each pulse is on the order of 500 microseconds and has an energy of up to 250 millijoules. Experience has shown that up to half of this energy can be lost to the absorption in the water, similar to the situation described above with respect to the Holmium laser.

This problem can be overcome using a short, low energy initiation pulse to create the vapor bubble. The minimum energy of this pulse would be on the order of 0.004 joules. This value can be derived using equation (1) above and considering that the typical delivery guide for a carbon dioxide laser has a diameter on the order of 1.0 mm and the absorption length of 10.6 micron radiation in water is on the order of 0.020 mm. The absorption length in water for the carbon dioxide laser is significantly shorter than for the Holmium laser output.

In accordance with the subject invention, the short, low energy initiation pulse would be followed by the longer, more energetic, full strength pulse. The second pulse will be triggered after the vapor bubble has been formed so that absorption in the fluid medium is minimized.

It should also be understood that the subject invention would have utility in situations where the absorption of the liquid medium is not based on the primary liquid molecules but on particulates dissolved in the liquid. For example, proteins dissolved in water or blood are highly absorptive of ultraviolet radiation. If a UV laser were used in the fluid environment having dissolved proteins, energy would be lost to the fluid. Once again this energy loss can be minimize by utilizing an initiation pulse to create a vapor bubble allowing the following pulse to directly reach the target.

In cases where the liquid medium does not strongly absorb the laser radiation, the subject invention will have less of an impact. Similarly, where the delivery end of the probe is placed into contact with the target, the energy should be directly delivered without an initiation pulse. However, in many present surgical procedures, operating wavelengths are being selected which are highly absorbed in the liquid medium. Moreover, it is often desirable and frequently required to space the delivery end of the fiber from the target. In the latter cases, the subject pulse format will substantially increase the amount of energy which can be delivered to the target.

While the subject invention has been described with reference to the preferred embodiments, various changes and modifications could be made therein, by one skilled in the art, without varying from the scope and spirit of the subject invention as defined by the appended claims. For example, the subject pulse format need not be limited to medical applications but can be useful in any situation where the target to be treated is immersed in an absorbing fluid.

I claim:

1. A method of irradiating a target with laser radiation, wherein said radiation is delivered to the target by a guide having a delivery end, and wherein the delivery end is spaced from the target, and wherein the space between the delivery end of the guide and the target is occupied with a liquid medium, and wherein the laser radiation has a wavelength which is absorbed in the liquid medium, said method comprising the steps of:

generating a first laser pulse having sufficient energy to form a vapor bubble in the liquid medium at the delivery end of the guide; and generating a second laser pulse a predetermined time after the first laser pulse, said predetermined time being selected to allow the vapor bubble to expand an amount sufficient to displace a substantial portion of the liquid medium from the space between the delivery end of the guide and the target so that said second laser pulse may be delivered to the target through the vapor bubble thereby minimizing the laser radiation absorbed by the liquid medium and maximizing the laser radiation reaching the target.

2. A method as recited in claim 3 wherein said steps of generating first and second pulses are sequentially repeated.

3. A method as recited in claim 1 wherein the energy of the first pulse exceeds an amount given by $$A*L*C*\Delta T$$

where A equals the cross-sectional area of the delivery end of the guide, L is the absorption length of the laser radiation in the liquid medium, C is the specific heat of the liquid medium and $\Delta T$ is the difference in temperature between the ambient temperature of the liquid medium and the boiling point temperature of the liquid medium.

4. A method as recited in claim 1 wherein the energy of the second pulse is at least an order of magnitude greater than the energy of the first pulse.

5. A method as recited in claim 1 wherein the first pulse is shorter than the second pulse.

6. A method as recited in claim 1 wherein the duration of the first pulse is less than 100 microseconds.

7. A method as recited in claim 1 wherein the duration of the first pulse is less than 30 microseconds.

8. A method as recited in claim 1 wherein the time period between the end of the first pulse and the beginning of the second pulse is at least 50 microseconds.

9. A method as recited in claim 1 wherein the time period between the end of the first pulse and the beginning of the second pulse is between 100 and 200 microseconds.

10. A laser system for irradiating a target with a laser beam, said target being immersed in a liquid medium, said system comprising:

a gain medium generating an output wavelength which is absorbed by the liquid medium;

means for exciting the gain medium to generate a laser beam;

means for guiding the laser beam from the gain medium to the target, said guide means having a delivery end positioned close to but spaced from the target; and means for controlling the excitation means, said control means functioning to cause a first laser pulse to be generated having an energy sufficient to form a vapor bubble in the liquid medium at the delivery end of the guide means and wherein said control means further functions to cause a second laser pulse to be generated a predetermined time after the first laser pulse, said predetermined time being selected to allow the vapor bubble to expand an amount sufficient to displace a substantial portion of the liquid medium from the space between the delivery end of the guide means and the target so that said second laser pulse may be delivered to the target through the vapor bubble thereby minimizing the laser radiation absorbed by the liquid medium and maximizing the laser radiation reaching the target.

11. A system as recited in claim 10 wherein the energy of the first pulse exceeds an amount given by $$A*L*C*\Delta T$$

where A equals the cross-sectional area of the delivery end of the guide, L is the absorption length of the laser radiation in the liquid medium, C is the specific heat of the liquid medium and $\Delta T$ is the difference in temperature between the ambient temperature of the liquid medium and the boiling point temperature of the liquid medium.

12. A system as recited in claim 10 wherein the energy of the second pulse is at least an order of magnitude greater than the energy of the first pulse.

13. A system as recited in claim 10 wherein the first pulse is shorter than the second pulse.

14. A system as recited in claim 10 wherein the duration of the first pulse is less than 100 microseconds.

15. A system as recited in claim 10 wherein the duration of the first pulse is less than 30 microseconds.

16. A system as recited in claim 10 wherein the time period between the end of the first pulse and the beginning of the second pulse is at least 50 microseconds.

17. A system as recited in claim 10 wherein the time period between the end of the first pulse and the beginning of the second pulse is between 100 and 200 microseconds.

18. A system as recited in claim 10 wherein said control means functions to generate a sequence of first and second pulses.

19. A system as recited in claim 10 wherein said gain medium is a rare earth doped crystal.

20. A system as recited in claim 10 wherein said gain medium is a material selected from the group consisting of Nd:YAG, Nd:YLF, Nd:YAP, Nd:YALO, Ho:YAG, Ho:YSGG, Ho:YLF and Er:YAG.

21. A system as recited in claim 10 wherein said gain medium is carbon dioxide.

22. A system as recited in claim 10 wherein said means for guiding the light is an optical fiber.

23. A medical laser system for treating tissue with a laser beam, said tissue being immersed in a liquid medium formed primarily of water, said system comprising:

a solid state gain medium generating an output wavelength between 1.0 and 3.0 microns;

a flashlamp for exciting the gain medium to generate a laser beam;

an optical fiber for guiding the laser beam from the gain medium to the tissue, said fiber having a delivery end positioned close to but spaced from the tissue to be treated; and means for controlling the flashlamp and functioning to sequentially generate a series of first and second laser pulses, wherein each said first laser pulse has an energy sufficient to form a vapor bubble in the liquid medium at the delivery end of the fiber and wherein each said second laser pulse is generated a predetermined time after the first laser pulse, said predetermined time being selected to allow the vapor bubble created by the first laser pulse to expand an amount sufficient to displace a substantial portion of the liquid medium from the space between the delivery end of the fiber and the tissue so that said second laser pulse may be delivered to the tissue through the vapor bubble thereby minimizing the laser radiation absorbed by the liquid medium and maximizing the laser radiation reaching the target.

24. A system as recited in claim 23 wherein the duration of the first pulse is less than 100 microseconds.

25. A system as recited in claim 24 wherein the time period between the end of the first pulse and the beginning of the second pulse is between 100 and 200 microseconds.

26. A system as recited in claim 24 wherein the time period between the end of the first pulse and the beginning of the second pulse is at least 50 microseconds.

27. A system as recited in claim 26 wherein gain medium is a material selected from the consisting of Nd:YAG, Nd:YLF, Nd:YAP, Nd:YALO, Ho:YAG, Ho:YSGG, Ho:YLF and Er:YAG.

28. A system as recited in claim 27 wherein the duration of the second pulse is at least 200 microseconds.

29. A method of irradiating a target with laser radiation, wherein said radiation is delivered to the target by a guide having a delivery end, and wherein the delivery end is spaced from the target, and wherein the space between the delivery end of the guide and the target is occupied with a liquid medium, and wherein the laser radiation has a wavelength which is absorbed in the liquid medium, said method comprising the steps of:

generating a first laser output having sufficient energy to form a vapor bubble in the liquid medium at the delivery end of the guide;

allowing the vapor bubble to expand an amount sufficient to displace a substantial portion of the liquid medium from the space between the delivery end of the guide and the target; and thereafter generating a second laser output, said second laser output being delivered to the target through the vapor bubble thereby minimizing the laser radiation absorbed by the liquid medium and maximizing the laser radiation reaching the target.

30. A method as recited in claim 29 wherein the energy of the first output exceeds an amount given by $$A*L*C*\Delta T$$

where A equals the cross-sectional area of the delivery end of the guide, L is the absorption length of the laser radiation in the liquid medium, C is the specific heat of the liquid medium and $\Delta T$ is the difference in temperature between the ambient temperature of the liquid medium and the boiling point temperature of the liquid medium.

31. A method as recited in claim 29 wherein the energy of the second laser output is at least an order of magnitude greater than the energy of the first output.

32. A method as recited in claim 29 wherein the first and second laser outputs are in the form of pulses and wherein the first pulse is shorter than the second pulse.

33. A method as recited in claim 32 wherein the duration of the first pulse is less than 100 microseconds.

34. A method as recited in claim 32 wherein the duration of the first pulse is less than 30 microseconds.

35. A method as recited in claim 32 wherein the time period between the end of the first pulse and the beginning of the second pulse is at least 50 microseconds.

36. A method as recited in claim 32 wherein the time period between the end of the first pulse and the beginning of the second pulse is between 100 and 200 microseconds.

37. A method as recited in claim 29 wherein said steps of generating first and second outputs are sequentially repeated.

* * * * *